United States Patent [19]

Jikihara et al.

[11] 4,163,661
[45] Aug. 7, 1979

[54] PHENOXYPHENOXY CROTONIC ACID DERIVATIVES AND HERBICIDAL COMPOSITION

[75] Inventors: Kazuo Jikihara, Kakegawa; Shigekazu Itoh; Shuichi Takayama, both of Shimizu; Koichi Sato; Ichiro Kimura, both of Shizuoka; Isao Chiyomaru, Shimizu, all of Japan

[73] Assignee: Kumiai Chemical Industry Co., Ltd., Tokyo, Japan

[21] Appl. No.: 919,272

[22] Filed: Jun. 26, 1978

[30] Foreign Application Priority Data

Oct. 31, 1977 [JP] Japan .................................. 52/130394
Feb. 14, 1978 [JP] Japan .................................. 53/15654

[51] Int. Cl.² .......................... C07C 69/76; A01N 9/24
[52] U.S. Cl. ....................................... 71/108; 560/62; 562/472
[58] Field of Search .......................... 562/472; 560/62; 71/108

[56] References Cited

U.S. PATENT DOCUMENTS 4,070,178  1/1978  Johnson et al. ...................... 562/472

FOREIGN PATENT DOCUMENTS 49-52525 of 1974 Japan .
49-54526 of 1974 Japan .
51-12924 of 1976 Japan .
52-33637 of 1977 Japan .

Primary Examiner—Robert Gerstl
Assistant Examiner—L. Hendriksen
Attorney, Agent, or Firm—Oblon, Fisher, Spivak, McClelland & Maier

[57] ABSTRACT

Trifluoromethylphenoxy phenoxy crotonic acid derivatives of the formula

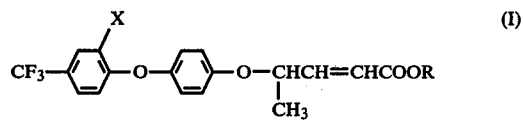

wherein X represents hydrogen or halogen atom, and R represents an alkyl, haloalkyl, alkenyl haloalkenyl or alkynyl group are disclosed. These compounds disclose herbicidal activity.

8 Claims, No Drawings

PHENOXYPHENOXY CROTONIC ACID DERIVATIVES AND HERBICIDAL COMPOSITION

DETAILED DESCRIPTION OF THE INVENTION

The present invention relates to trifluoromethylphenoxy phenoxy crotonic acid derivatives having the formula

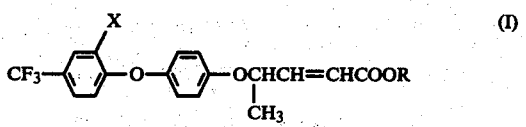

wherein X represents hydrogen or halogen atom and R represents an alkyl, haloalkyl, alkenyl, haloalkenyl or alkynyl group; and a preparation thereof and a herbicidal composition comprising the same.

Recently, many herbicides have been proposed and practically used to contribute for elimination of agricultural labour works.

Thus, various problems on herbicidal effects and safety of the herbicides have been found in the practical applications.

It has been awaited to find improved herbicides which have no adverse effect to the object plants and effective to noxious weeds in a small dose of the active ingredient and significantly safe without any environmental pollution.

The inventors have synthesized various phenoxyphenoxy crotonic acid derivatives so as to find satisfactory herbicides and have studied herbicidal effects thereof.

The novel compounds of trifluoromethylphenoxy phenoxy crotonic acid derivatives having the formula (I) of the present invention have superior herbicidal activity to gramineous weeds such as barnyard grass, crab grass and Johnson grass in comparison with the compounds described in Japanese Unexamined Patent Publication No. 33637/1977 such as methyl 2-[4-4(trifluoromethylphenoxy)phenoxy]crotonate, ethyl, 2-[4-(4-trifluoromethyl-2-chlorophenoxy)phenoxy]crotonate, ethyl, γ-[4-(4-trifluoromethylphenoxy)phenoxy]valerylate and ethyl, γ-[4-(4-trifluoromethyl-2-chlorophenoxy)phenoxy]valerylate. The novel compounds of the present invention have superior residual activity in soil in a soil treatment in comparison with γ-[4-(4-trifluoromethylphenoxy)phenoxy]propionic acid derivatives disclosed in Japanese Unexamined Patent Publication No. 12924/1976.

The novel compounds of the present invention also have excellent effects such as a long suppression of weeds in later emergence; a long suppression of recovery from an incomplate suppression of weeds in a foliage treatment; growth control of grown weeds and excellent stability to the factors for varying the activity caused by rain-fall, atmospheric moisture and high temperature to impart stable activity.

The novel compounds of the present invention have methyl group at γ-position of the trifluoromethylphenoxy phenoxy crotonic acid compounds, whereby the special herbicidal effect especially, significant herbicidal effect to gramineous weeds such as johnson grass, dent foxtail, barnyard grass and large crab grass can be imparted.

The novel compounds of the present invention have significant selectivity without phytotoxicity to broad leaf crop plants such as radish, soybean, pea-nut, cotton, flax, beet, pimento and sunflower, but completely control gramineous weeds barnyard grass, large crab grass, jonson grass, wild sorghum, quack grass, dent foxtail and paspalum grass.

The novel compounds of the present invention can be applied as herbicides by desirable methods in every seasons such as the soil treatment and the foliage treatment in post-emergence and pre-emergence.

The significant characteristics of the novel compounds are to have significant herbicidal effect in the foliage treatment, for example, to completely control johnson grass in 5 leaf-stage or more.

Typical gramineous weeds which are effectively controlled by the herbicides of the present invention are as follows: johnson grass, quack grass, para-grass, southern sandbar, finger grass, bermuda grass, crowfoot grass, large crab grass, crab grass, barnyard grass, jungle rice, cattail grass, goose grass, cogon grass, wrinkle grass, southern cut grass, Bearded splangle top, red splangle top, mexican splangle top, brown top panicum, sour paspalum, water paspalum, natal grass, raoul grass, green foxtail, bristly foxtail, yellow foxtail.

The trifluoromethylphenoxy phenoxy crotonic acid derivatives having the formula (I) can be produced by the following processes.

The trifluoromethylphenoxy phenoxy crotonic acid derivatives having the formula

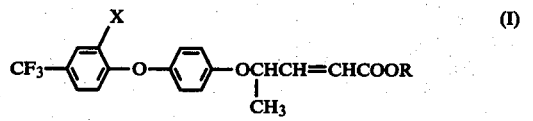

wherein X represents hydrogen or halogen atom; and R represents an alkyl, haloalkyl, alkenyl, haloalkenyl or alkynyl group can be produced in high yield by reacting a trifluoromethylphenoxy phenol derivative having the formula

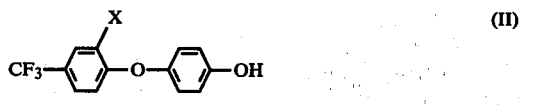

wherein X is defined above with γ-halogen-γ-methylcrotonic acid derivative having the formula

wherein $X_1$ represents a halogen atom and R is defined above in a reaction medium in the presence of a base at 0° to 150° C. for 1 to 20 hours.

Suitable bases include alkali metal hydroxides such as sodium hydroxide or potassium hydroxide; alkali metal carbonates such as sodium carbonate, potassium carbonate, sodium bicarbonate; alcoholates such as sodium ethylate and tertiary amines such as triethyl amine, dimethyl aniline or pyridine, etc.

Suitable reaction media include water, acetone, methylethyl ketone, methanol, ethanol, isopropanol, butanol, dimethylformamide, dimethylsulfoxide, tetrahydrofuran, benzene, toluene, xylene, chlorobenzene, chloroform, carbon tetrachloride, dichloroethane etc.

Certain examples for producing the compounds by this process will be described.

PREPARATION 1

Ethyl γ-methyl-γ[4-(4'-trifluoromethylphenoxy)phenoxy]crotonate

To 70 ml of ethanol was added 0.9 g (0.039 mole) of sodium (metal) to prepare sodium ethylate and 8.9 g (0.035 mole) of 4-(4'-trifluoromethylphenoxy)phenol was added to the sodium ethylate and then, 8.0 g (0.039 mole) of ethyl γ-bromo-γ-methyl crotonate was added. The mixture was refluxed to react them for 4 hours. The reaction mixture was extracted with toluene and the toluene phase was successively washed with water a diluted hydrochloric acid and water and dried with anhydrous sodium sulfate and the solution was concentrated to distil off toluene. The residue was purified by a vacuum distillation to give 10.8 g (yield: 81.5%) of pale yellow viscours liquid having a boiling point of 173° C./0.01 mmHg and $n_D^{20}$ 1.5175.

PREPARATION 2

Isoprophyl γ-methyl-γ-[4-(4'-trifluoromethylphenoxy)phenoxy]-crotonate

To 150 ml dimethylformamide was dissolved 25.4 g (0.1 mole) of 4-(4'-trifluoromethylphenoxy)phenol and 19.3 g (0.14 mole) of sodium carbonate and 27.0 g (0.1 mole) of isoprophyl γ-bromo-γ-methyl crotonate were added under stirring to react them at 100° C. for 6 hours.

After cooling the reaction mixture, it was poured into water and the reaction product was extracted with dichloromethane and successively washed with water a diluted hydrochloric acid and water and dried with anhydrous sodium sulfate and the solution was concentrated to distil off dichloromethane.

The residue was purified by a vacuum distillation to give 33.6 g (yield: 85%) of pale yellow liquid having a boiling point of 158° C./0.015 mmHg and a refractive index of $n_D^{20}$ 1.5134.

PREPARATION 3

Allyl γ-methyl-γ-[4-(4'-trifluoromethylphenoxy)phenoxy crotonate

To 300 ml of anhydrous toluene was dissolved 25.4 g (0.1 mole) of 4-(4'-trifluoromethylphenoxy)phenol and 8.8 g (0.11 mole) of pyridine and the solution was cooled in ice water and 21 g (0.12 mole) of allyl γ-chloro-γ-methyl crotonate was added. The mixture was heated at room temperature for 2 hours and then at 40° C. for 2 hours to react them and washed with water and dried with anhydrous sodium sulfate and the solution was concentrated to distil off toluene.

The residue was purified by a vacuum distillation to give 34.9 g (yield: 89%) of pale yellow liquid having a boiling point of 172° to 174° C./0.015 mmHg and a refractive index of $n_D^{20}$ 1.5218.

In accordance with said process, except using the following starting compound instead of allyl γ-chloro-γ-methyl crotonate and reacting it with 4-[4'-trifluoromethylphenoxy)phenol in ethanol in the presence of potassium carbonate, the following corresponding products were obtained.

| Starting compound | Products |
|---|---|
| methyl γ-bromo-γ-methyl crotonate | methyl γ-methyl-γ-[4-(4'-trifluoromethylphenoxy) phenoxy]crotonate |
| ethyl γ-bromo-γ-methyl crotonate | ethyl γ-methyl-γ-[4-(4'-trifluoromethylphenoxy) phenoxy]crotonate |
| propyl γ-bromo-γ-methyl crotonate | propyl γ-methyl-γ-[4-(4'-trifluoromethylphenoxy) phenoxy]crotonate |
| butyl γ-bromo-γ-methyl crotonate | butyl γ-methyl-γ-[4-(4'-trifluoromethylphenoxy) phenoxy]crotonate |
| allyl γ-bromo-γ-methyl crotonate | allyl γ-methyl- γ-[4-(4'-trifluoromethylphenoxy) phenoxy]crotonate |
| chloroethyl γ-bromo-γ-methyl crotonate | chloroethyl γ-methyl -methyl-γ-[4-(4'-trifluoromethylphenoxy) phenoxy]crotonate |
| propargyl γ-bromo-γ-methyl crotonate | propargyl γ-methyl-γ-[4-(4'-trifluoromethylphenoxy) phenoxy]crotonate |

In accordance with said process except reacting γ-bromo-γ-ethyl crotonate with 4-(2'-chloro-4'-trifluoromethylphenoxy)phenol in ethanol in the presence of potassium carbonate ethyl γ-methyl-γ-[4-(2'-chloro-4'-trifluoromethylphenoxy)phenoxy]crotonate was obtained.

The trifluoromethylphenoxy phenoxy crotonic acid derivatives having the formula (I) can be also produced by reacting a trifluoromethylphenoxy phenoxy crotonic acid derivative having the formula

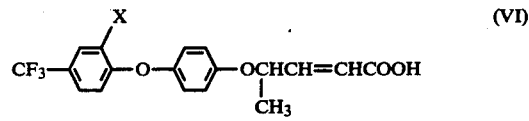

(VI)

wherein X represents hydrogen or halogen atom, with an alcohol having the formula

ROH wherein R represents an alkyl, haloalkyl, alkenyl, haloalkenyl or alkynyl group, in the presence of a catalyst such as sulfuric acid hydrochloric acid; an aromatic sulfonic acid such as benzenesulfonic acid, toluenesulfonic acid or β-naphthalenesulfonic acid; an anhydrous sulfate such as anhydrous copper sulfate or anhydrous iron sulfate; phosphorus oxychloride, phosphoric acid anhydride, boron trifluoride or acidic ion-exchanger at 20° to 150° C. or under refluxing for 1 to 20 hours.

Certain examples for producing the compounds by the process will be described.

PREPARATION 4

Methyl γ-methyl-γ-[4(4'-trifluoromethylphenoxy)phenoxy]crotonate

A mixture of 70.0 g (0.2 mole) of γ-methyl-γ-[4(4'-trifluoromethylphenoxy)phenoxy]crotonic acid, 200 ml of methanol and 10 g of conc. sulfuric acid was refluxed for 4 hours and then, concentrated by distilling off about ½ of methanol. Then, 300 ml of water was added to dilute it and the resulting oily product was extracted with ether. The ether phase was dried with anhydrous sodium sulfate and ether was distilled off. The residual oily product was purified by vacuum distillation to give 65.9 g (yield: 90.0%) of pale yellow viscous liquid having a boiling point of 157° to 162° C./0.015 mmHg and a refractive index of $n_D^{20}$ 1.5238.

In accordance with said process except reacting γ-methyl-γ-[4-(4'-trifluoromethylphenoxy)phenoxy]crotonic acid with methanol, ethanol, propanol, butanol, allyl alcohol or propargyl alcohol in the presence of the catalyst of paratoluenesulfonic acid, the following products were obtained.

| Alcohol | Product |
|---|---|
| methanol | methyl γ-methyl-γ-[4-(4'-trifluoromethyl-phenoxy) phenoxy]crotonate |
| ethanol | ethyl γ-methyl-γ-[4-(4'-trifluoromethyl-phenoxy) phenoxy]crotonate |
| propanol | propyl γ-methyly-[4-(4'-trifluoromethyl-phenoxy) phenoxy]crotonate |
| butanol | butyl γ-methyl-γ-[4-(4'-trifluoromethyl-phenoxy) phenoxy]crotonate |
| allyl alcohol | allyl γ-methyl-γ-[4-(4'-trifluoromethyl-phenoxy) phenoxy]crotonate |
| propargyl alcohol | propargyl γ-methyl-γ-[4-(4'-trifluoromethyl-phenoxy) phenoxy]crotonate |

In accordance with said process except reacting γ-methyl-γ-[4-(4'-trifluoromethylphenoxy)phenoxy]crotonic acid with ethanol in the presence of the catalyst of paratoluenesulfonic acid, ethyl γ-methyl-γ-[4-(2'-chloro-4'-trifluoromethylphenoxy)phenoxy]crotonate was obtained.

The trifluoromethylphenoxy phenoxy crotonic acid derivatives having the formula (I) can be also produced by reacting a trifluoromethylphenoxy phenoxy crotonic acid derivative having the formula

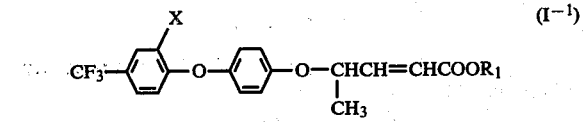

(I-1)

wherein R₁ is different from R₂ and represents an alkyl, haloalkyl, alkenyl, haloalkenyl or alkynyl group with an alcohol having the formula

R₂OH wherein R₂ is different from R₁ and represents an alkyl, haloalkyl, alkenyl, haloalkenyl, or alkynyl group in the absence or the presence of a catalyst such as an acid such as sulfuric acid or paratoluenesulfonic acid; an alcoholate such as sodium ethylate or potassium butyrate; pyridine or basic ion exchange resin at 0° to 150° C. for 1 to 20 hours, in an interesterification.

Certain examples for producing the compound by this process will be described.

PREPARATION 5

Isopropyl γ-methyl-γ-[4-(4'-trifluoromethylphenoxy)phenoxy)-crotonate

To 70 ml of isopropyl alcohol was added 19.0 g (0.05 mole) of ethyl γ-methyl-γ-[4-(4'-trifluoromethylphenoxy)phenoxy]crotonate and 3 g of sulfuric acid. The mixture was refluxed for 15 hours to react them, and concentrated to distil off about 50 ml of isopropyl alcohol. Then, 150 ml of water was added and the resulting oil was extracted with ether and the ether phase was washed with water and dried with anhydrous sodium sulfate and ether was distilled off.

The residual oily product was purified by a vacuum distillation to give 14.2 g (yield: 72.3%) of pale yellow viscours liquid having a boiling point of 158°/0.015 mmHg and a refractive index of n_D²⁰ 1.5134.

In accordance with said process except reacting ethyl γ-methyl-γ-[4-(4'-tfifluoromethylphenoxy)phenoxy]-crotonate with butyl alcohol instead of butyl γ-methyl-γ-[4-(4'-trifluoromethylphenoxy)phenoxy]crotonate was obtained.

The trifluoromethylphenoxy phenoxy crotonic acid derivatives having the formula (I) can be produced by reacting trifluoromethylphenoxy phenoxy crotonic acid halide having the formula

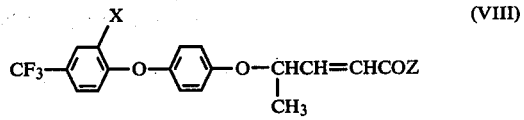

(VIII)

wherein X represents hydrogen or halogen atom; and Z represents a halogen atom, with an alcohol having the formula

ROH  (V)

wherein R represents an alkyl, haloalkyl, alkenyl, haloalkenyl or alkynyl group in the absence or in the presence of a dehydrogenhalide agent of a base in a reaction medium or excess of the alcohol having the formula ROH or without a reaction medium, at −10° to 150° C. for 1 to 20 hours.

Suitable dehydrogenhalide agents of inorganic or organic bases include alkali metal hydroxides such as sodium hydroxide or potassium hydroxide; alkali metal carbonates such as sodium carbonate, potassium carbonate or sodium bicarbonate; alcoholates such as sodium ethylate; and tertiary amines such as triethyl amine, dimethyl aniline or pyridine.

Suitable reaction media include acetone, methyl ethyl ketone, dimethylformamide, dimethylsulfoxide, tetrahydrofuran, benzene, toluene, xylene, chlorobenzene, chloroform, carbon tetrachloride and dichloroethane.

Certain examples for producing the compounds by this process will be described.

PREPARATION 6

Ethyl γ-methyl-γ-[4-(4'-trifluoromethylphenoxy)phenoxy]-crotonate

To 200 ml of anhydrous ethyl alcohol was added 37 g (0.1 mole) of γ-methyl-γ-[4-(4'-trifluoromethylphenoxy)phenoxy]crotonic acid chloride. The mixture was kept at room temperature for 1 day to react them and then, ethyl alcohol was distilled off.

The residue was purified by a vacuum distillation to give 34.9 g (yield: 92.5%) of pale orange liquid having a boiling point of 173° C./0.01 mmHg and a refractive index of n_D²⁰ 1.5175.

PREPARATION 7 n-Butyl γ-methyl-γ-[4-(4'-trifluoromethylphenoxy)phenoxy]-crotonate

To 250 ml of n-butyl alcohol was added 40.6 g (0.1 mole) of γ-methyl-γ-[4-(4'-trifluoromethylphenoxy)phenoxy]crotonic acid bromide. Then, the mixture was gradually heated to 60° C. and kept at 60° C. for 5 hours to react them, and n-butyl alcohol was distilled off.

The residue was purified by a vacuum distillation to give 36.1 g (yield: 88.8%) of a pale yellow viscous liquid having a boiling point of 180° to 182° C./0.02 mmHg and a refractive index of $n_D^{20}$ 1.5137.

PREPARATION 8

Methyl γ-methyl-γ-[4-(4'-trifluoromethylphenoxy)phenoxy]-crotonate

A mixture of 74 g (0.02 mole) of γ-methyl-γ-[4-(4'-tri-fluromethylphenoxy)phenoxy]crotonic acid and 30 ml of thionyl chloride was refluxed for 6 hours to react them. Then, excess of thionyl chloride was distilled off and 50 ml of methanol was added to the residual acid chloride. The mixture was refluxed for 5 hours to react them and methanol was distilled off.

The residue was purified by a vacuum distillation to give 6.4 g (yield: 87.3%) of pale yellow liquid having a boiling point of 157° to 162° C./0.015 mmHg and a refractive index of $n_D^{20}$ 1.5238.

In accordance with said process except reacting γ-methyl-γ-[4-(4'-trifluoromethylphenoxy)phenoxy]crotonic acid with thionyl chloride and distilling off excess of thionyl chloride and reacting propyl alcohol, butyl alcohol, allyl alcohol, propargyl alcohol, or chloroethyl alcohol instead of methanol, the following corresponding products were obtained.

| Alcohol | Product |
| --- | --- |
| propyl alcohol | propyl γ-methyl-γ-[4-(4'-trifluoromethyl-phenoxy) phenoxy]crotonate |
| butyl alcohol | butyl γ-methyl-γ-[4-(4'-trifluoromethyl-phenoxy) phenoxy]crotonate |
| allyl alcohol | allyl γ-methyl-γ-[4-(4'-trifluoromethyl-phenoxy) phenoxy]crotonate |
| propargyl alcohol | propargyl γ-methyl-γ-[4-(4'-trifluoromethyl-phenoxy) phenoxy]crotonate |
| chloroethyl alcohol | chloroethyl γ-methyl-γ-[4-(4'-trifluoro-methylphenoxy) phenoxy]crotonate |

The typical compounds obtained by said processes will be exemplified. The compound numerals are referred in the following description.

COMPOUND NO. 1

Methyl γ-methyl-γ-[4-(4'-trifluoromethylphenoxy)-phenoxy]crotonate.
  b.p.: 157° to 162° C./0.015 mmHg;
  $n_D^{20}$: 1.5238

COMPOUND NO. 2

Ethyl γ-methyl-γ-[4-(4'-trifluoromethylphenoxy)-phenoxy]crotonate
  b.p.: 173° C./0.01 mmHg;
  $n_D^{20}$: 1.5175

COMPOUND NO. 3

Isopropyl γ-methyl-γ-[4-(4'-trifluoromethylphenoxy)phenoxy]crotonate.
  b.p.: 158° C./0.015 mmHg;
  $n_D^{20}$: 1.5134

COMPOUND NO. 4 n-Butyl γ-methyl-γ-[4-(4'-trifluoromethylphenoxy)-phenoxy]crotonate.
  b.p.: 180° to 182° C./0.02 mmHg;
  $n_D^{20}$: 1.5137

COMPOUND NO. 5

Isobutyl γ-methyl-γ-[4-(4'-trifluoromethylphenoxy)-phenoxy]crotonate.
  b.p.: 172° to 174° C./0.007 mmHg;
  $n_D^{20}$: 1.5100

COMPOUND NO. 6

Ethyl γ-methyl-γ-[4-(4'-trifluoromethyl-2-chloro-phenoxy)phenoxy]crotonate.
  b.p.: 175° to 185° C./0.007 mmHg;
  $n_D^{20}$: 1.5283

COMPOUND NO. 7

Allyl γ-methyl-γ-[4-(4'-trifluoromethylphenoxy)-phenoxy]crotonate.
  b.p.: 172° to 174° C./0.015 mmHg;
  $n_D^{20}$: 1.5218

COMPOUND NO. 8

Propargyl γ-methyl-γ-[4-(4'-trifluoromethylphenoxy)phenoxy]crotonate.
  b.p.: 180° to 181° C./0.015 mmHg;
  $n_D^{20}$: 1.5310

COMPOUND NO. 9

2-chloroethyl γ-methyl-γ-[4-(4'-trifluoromethylphenoxy)phenoxy]crotonate.
  b.p.: 192° C./0.007 mmHg;
  $n_D^{20}$: 1.5284

COMPOUND NO. 10

2-chloroallyl γ-methyl-γ-[4-(4'-trifluoromethylphenoxy)phenoxy]crotonate.
  b.p.: 190° to 193° C./0.01 mmHg;
  $n_D^{20}$: 1.5310

COMPOUND NO. 11

Sec-butyl γ-methyl-γ-[4-(4'-trifluoromethylphenoxy)phenoxy]crotonate:
  b.p.>140° C./0.07 mmHg
  $n_D^{20}$: 1.5112

COMPOUND NO. 12

Isoamyl γ-methyl-γ-[4-(4'-trifluoromethylphenoxy)-phenoxy]crotonate.
  b.p.>140° C./0.07 mmHg
  $n_D^{20}$: 1.5095

COMPOUND NO. 13 n-Octyl γ-methyl-γ-[4-(4'-trifluoromethylphenoxy)-phenoxy]crotonate:
  b.p.>140° C./0.07 mmHg
  $n_D^{20}$: 1.5045

COMPOUND NO. 14

1-Methylallyl γ-methyl-γ-[4-(4'-trifluoromethyl-phenoxy)phenoxy]crotonate:
  b.p.>140° C./0.07 mmHg
  $n_D^{20}$: 1.5176

COMPOUND NO. 15

2-Hexenyl γ-methyl-γ-[4-(4'-trifluoromethylphenoxy)phenoxy]crotonate:
  b.p.>180° C./0.07 mmHg
  $n_D^{20}$: 1.5153

COMPOUND NO. 16

2-Bromoethyl γ-methyl-γ-[4-(4'-trifluoromethylphenoxy)phenoxy]crotonate:
b.p.>140° C./0.07 mmHg
$n_D^{20}$: 1.5360

COMPOUND NO. 17

3-Chloropropyl γ-methyl-γ-[4-(4'-trifluoromethylphenoxy)phenoxy]crotonate:
b.p.>140° C./0.07 mmHg
$n_D^{20}$: 1.5240

COMPOUND NO. 18

2,2,2-trichloroethyl γ-methyl γ-[4-(4'-trifluoromethylphenoxy)phenoxy]crotonate:
b.p.>155° C./0.07 mmHg
$n_D^{20}$: 1.5320

COMPOUND NO. 19

Methyl γ-methyl-γ-[4-(4'-trifluoromethyl-2'-chlorophenoxy)phenoxy]crotonate:
b.p.>150° C./0.07 mmHg
$n_D^{20}$: 1.5323

COMPOUND NO. 20

Isopropyl γ-methyl-γ-[4-(4'-trifluoromethyl-2'-chlorophenoxy)phenoxy]crotonate:
b.p.>150° C./0.07 mmHg
$n_D^{20}$: 1.5227

COMPOUND NO. 21 n-Butyl γ-methyl-γ-[4-(4'-trifluoromethyl-2'-chlorophenoxy)phenoxy]crotonate:
b.p.>150° C./0.07 mmHg
$n_D^{20}$: 1.5222

COMPOUND NO. 22

Allyl γ-methyl-γ-[4-(4'-trifluoromethyl-2'-chlorophenoxy)phenoxy]crotonate:
b.p.>150° C./0.07 mmHg
$n_D^{20}$: 1.5328

COMPOUND NO. 23

Propargyl γ-methyl-γ-[4-(4'-trifluoromethyl-2'-chlorophenoxy)phenoxy]crotonate:
b.p.>150° C./0.07 mmHg
$n_D^{20}$: 1.5376

COMPOUND NO. 24

2-Bromoethyl γ-methyl-γ-[4-(4'-trifluoromethyl-2'-chlorophenoxy)phenoxy]crotonate:
b.p.>150° C./0.07 mmHg
$n_D^{20}$: 1.5436

COMPOUND NO. 25

3-Chloropropyl γ-methyl-γ-[4-(4'-trifluoromethyl-2'-chlorophenoxy)phenoxy]crotonate:
b.p.>150° C./0.07 mmHg
$n_D^{20}$: 1.5324

COMPOUND NO. 26

Ethyl γ-methyl-γ-[4-(4'-trifluoromethyl-2'-bromophenoxy)phenoxy]crotonate:
b.p.>150° C./0.07 mmHg
$n_D^{20}$: 1.5341

The following compounds are also effective as herbicides γ-methyl-γ-[4-(4'-trifluoromethylphenoxy)phenoxy]crotonic acid of n-propyl ester, sec-butyl ester, tert-butyl ester, n-amyl ester, i-amyl ester, n-hexyl ester, n-octyl ester, vinyl ester, 2-methylallyl ester, butenyl ester, 2-propylallyl ester, 2-hexenyl ester, 2-bromoethyl ester, trichloroethyl ester, 1-chloro-2-propyl ester, 1,3-dichloro-2-propyl ester and 3-bromopropyl ester.

γ-methyl-γ-[4-(4'-trifluoromethyl-2-chlorophenoxy)phenoxy]crotonic acid or γ-methyl-γ-[4-(4'-trifluoromethyl-2-bromophenoxy)phenoxy]crotonic acid of methyl ester, ethyl ester, n-propyl ester, i-propyl ester, n-butyl ester, isobutyl ester, sec-butyl ester, tert-butyl ester, amyl ester, allyl ester, propargyl ester, chloroethyl ester, bromoethyl ester, trichloroethyl ester, 1-chloro-2-propyl ester or 1,3-dichloro-2-propyl ester.

The novel compounds of the present invention produced by said syntheses have significant herbicidal effect and non-phytotoxicity to many crop plants and can be applied to up-land, paddy fields, orchards, forests and non-cultured grounds by the soil treatment or the foliage treatment under selecting suitable method of application and suitable dose of the active ingredient.

The dose of the active ingredient of the compound of the present invention is depending upon a weather condition, a soil condition, a form of the composition, a season of the application and a method of the application and kinds of crop plants and kinds of weeds and it is usually in a range of 0.01 to 10 kg preferably 0.1 to 5 kg especially 0.5 to 3 kg per 1 hectare in the soil treatment and it is usually applied in a concentration of 10 to 10,000 ppm preferably 100 to 5,000 ppm especially 250 to 3,000 ppm of the active ingredient.

When the compound of the present invention is used as the herbicide, the compound can be used in the original form and also in the form of compositions such as granules, wettable powder, dusts, emulsifiable concentrates, fine power, floables, suspensions, etc to impart superior effect.

In the preparation of the herbicidal compositions, the compound of the present invention can be uniformly mixed with or dissolved in suitable adjuvants such as solid carrier such as talc, bentonite, clay, kaolin, diatomaceous earth, silica gel, vermiculite, lime, siliceous sand, ammonium sulfate or urea; liquid carriers such as alcohols, dioxane, acetone, cyclohexanone, methyl naphthalene or dimethylformamide; surfactants as emulsifiers dispersing agents or wetting agents such as alkyl sulfate, alkylsulfonate, polyoxyetheyleneglycol ethers, polyoxyethylenealkylaryl ethers such as polyoxyethylenenonylphenol ether or polyoxyethylenesorbitane monoalkylate; and carboxymethyl cellulose, gum arabic and other adjuvants.

The amounts of the active ingredients, adjuvants and additives in the herbicidal compositions of the present invention will be further illustrated.

WETTABLE POWDER

Active ingredient: 5 to 95 wt. % preferably 20 to 50 wt. %
Surfactant: 1 to 20 wt. % preferably 5 to 10 wt. %
Solid carrier: 5 to 85 wt. % preferably 40 to 70 wt. %
The active ingredient is admixed with the solid carrier and the surfactant and the mixture is pulverized.

EMULSIFIABLE CONCENTRATE

Active ingredient: 5 to 95 wt. % preferably 20 to 70 wt. %
Surfactant: 1 to 40 wt. % preferably 5 to 20 wt. %

Liquid carrier: 5 to 90 wt. % preferably 30 to 60 wt. %

The active ingredient is dissolved in the liquid carrier and the surfactant is admixed.

DUST

Active ingredient: 0.5 to 10 wt. % preferably 1 to 5 wt. %

Solid carrier: 99.5 to 90 wt. % preferably 99 to 95 wt. %

The active ingredient is mixed with fine solid carrier and the mixture is pulverized.

GRANULE

Active ingredient: 0.5 to 40 wt. % preferably 2 to 10 wt. %

Solid carrier: 99.5 to 60 wt. % preferably 98 to 90 wt. %

The active ingredient is sprayed on the solid carrier or further coated with the solid carrier to form the granule.

The other herbicides can be incorporated in the herbicidal composition of the present invention.

Suitable additional herbicides include; carboxylic acid type compounds such as 2,3,6-trichlorobenzoic acid and salts thereof, 2,3,5,6-tetrachlorobenzoic acid and salts thereof, 2-methoxy-3,5,6-trichlorobenzoic acid and salts thereof, 2-methoxy-3,6-dichlorobenzoic acid and salts thereof, 2-methyl-3,6-dichlorobenzoic acid and salts thereof, 2,3-dichloro-6-methylbenzoic acid and salts thereof, 2,4-dichlorophenoxyacetic acid and salts and esters thereof, 2,4,5-trichlorophenoxyacetic acid and salts and esters thereof, 2-methyl-4-chlorophenoxyacetic acid and salts and esters thereof, α-(2,4,5-tri-chlorophenoxy)propionic acid and salts and esters thereof, 2-(2,4-dichlorophenoxy)butyric acid and salts and esters thereof, 4-(2-methyl-4-chlorophenoxy)-butyric acid and salts and esters thereof, 2,3,6-trichlorophenylacetic acid and salts thereof, 3,6-endoxohexahydrophthalic acid, dimethyl 2,3,5,6-tetrachloroterephthalate, trichloroacetic acid and salts thereof, 2,2-dichloropropionic acid and salts thereof and 2,3-dichloroisobutyric acid and salts thereof; and carbamic acid type compounds such as ethyl N,N-di(n-propyl)-thiolcarbamate, propyl N,N,-di(n-propyl)thiolcarbamate, ethyl N-ethyl-N-(n-butyl)thiolcarbamate, propyl N-ethyl-N-(n-butyl)thiolcarbamate, 2-chloroallyl N,N-diethyl dithiocarbamate, N-methyl dithiocarbamate, S-ethyl hexahydro-1H-azepine-1-carbothioate, S-4-chlorobenzyl N,N-diethyl thiolcarbamate, S-benzyl N,N-di-sec-butyl thiolcarbamate, isopropyl N-phenyl carbamate, isopropyl N-(m-chlorophenyl)carbamate, 4-chloro-2-butyl N-(m-chlorophenyl)carbamate, methyl N-(3,4-dichlorophenyl)carbamate and methyl sulfanyl carbamate; phenol type compounds such as dinitro-O-(sec-butyl)phenol and salts thereof and pentachlorophenol and salts thereof; urea type compounds such as 3-(3,4-dichlorophenyl)-1,1-dimethyl urea, 3-phenyl-1,1-dimethyl urea, 3-(3,4-dichlorophenyl)-3-methoxy-1,1-dimethylurea, 3-(4-chlorophenyl)-3-methoxy-1,1-dimethylurea, 3-(3,4-dichlorophenyl)-1-n-butyl-1-methylurea, 3-(3,4-dichlorophenyl)-1-methoxy-1-methylurea, 3-(4-chlorophenyl)-1-methoxy-1-methylurea, 3-(3,4-dichlorophenyl)-1,1,3-trimethylurea, 3-(3,4-dichlorophenyl)-1,1-diethylurea, 1-(2-methylcyclohexyl)-3-phenylurea, 1-(5-t-butyl-1,3,4-triadiazol-2-yl)-1,3-dimethylurea, 3-(3-chloro-4-methylphenyl)-1,1-dimethylurea, 3-(3-chloro-4-methoxyphenyl)-1,1-dimethylurea and dichloralurea; triazine type compounds such as 2-chloro-4,6-bis(ethylamino)-s-triazine, 2-chloro-4-ethylamino-6-isopropyl-amino-s-triazine, 2-chloro-4,6-bis(methoxypropylamino)-s-triazine, 2-methoxy-4,6-bis(isopropylamino)-s-triazine, 2-methylmercapto-4,6-bis(isopropylamino)-s-triazine, 2-methylmercapto-4,6-bis(ethylamino)-s-triazine, 2-methylmercapto-4-ethylamino-6-isopropylamino-s-triazine, 2-chloro-4,6-bis(isopropylamino)-s-triazine, 2-methoxy-4,6-bis(ethylamino)-s-triazine, 2-methoxy-4-ethylamino-6-isopropylamino-s-triazine, 2-methylmercapto-4-(2-methoxyethylamino)-6-isopropylamino-s-triazine, 2-(4-chloro-6-ethylamino-s-triazine-2-yl)amino-2-methyl propionitrile, 4-amino-6-t-butyl-3-methylthio-1,2,4-triazine-5-(4H)-one, and 3-cyclohexyl-6-dimethylamino-1-methyl-s-triazine-2,4-(1H, 3H)dione; ether type compounds such as 2,4-dichloro-4'-nitrodiphenyl ether, 2,4,6-trichloro-4'-nitrodiphenyl ether, 2,4-dichloro-6-fluoro-4'-nitrodiphenyl ether, 3-methyl-4'-nitrodiphenyl ether, 3,5-dimethyl-4'-nitrodiphenyl ether, 2,4'-dinitro-4-trifluoromethyl diphenyl ether, 2,4-dichloro-3'-methoxy-4'-nitrodiphenyl ether, 2-chloro-4-trifluoromethyl-4'-nitrodiphenyl ether, 2-chloro-4-trifluoromethyl-3'-ethoxy-4'-nitrodiphenyl ether, 2-chloro-4-trifluoromethyl-3'-carbethoxy-4'-nitrodiphenyl ether and 2-chloro-4-trifluoromethyl-3'-(1-carbethoxy)ethoxy-4'-nitrodiphenyl ether;

anilide type compounds such as N-(3,4-dichlorophenyl)propionamide, N-(3,4-dichlorophenyl)methacrylamide, N-(3-chloro-4-methylphenyl)-2-methylpentamide, N-(3,4-dichlorophenyl)-trimethyl acetamide, N-(3,4-dichlorophenyl)-α,α-dimethyl valeramide, N-isoprophyl-N-phenylchloroacetamide, N-n-butoxymethyl-N-(2,6-diethylphenyl) chloroacetamide and N-n-methoxymethyl-N-(2,6-diethylphenyl)chloroacetamide;

uracil type compounds such as 5-bromo-3-sec-butyl-6-methyluracil, 5-bromo-3-cyclohexyl-1,6-dimethyluracil, 3-cyclohexyl-5,6-trimethyleneuracil, 5-bromo-3-isopropyl-6-methyluracil, and 3-tert.-butyl-5-chloro-6-methyluracil;

nitrile type compounds such as 2,6-dichlorobenzonitrile, diphenylacetonitrile, 3,5-dibromo-4-hydroxybenzonitrile, and 3,5-diiodo-4-hydroxybenzonitrile;

others such as 2-chloro-N,N-diallylacetamide, N-(1,1-dimethyl-2-propyl)-3,5-dichlorobenzamide, maleic acid hydrazide, 3-amino-1,2,4-triazole, mono-sodium methane arsonate, di-sodium methane arsonate, N,N-dimethyl-α,α-diphenyl acetamide, N,N-di(n-propyl)-2,6-dinitro-4-trifluoromethyl aniline, N,N-di(n-propyl)-2,6-dinitro-4-methyl aniline, N,N-di(n-propyl)-2,6-dinitro-4-methylsulfonyl aniline, O-(2,4-dichlorophenyl)-O-methylispropyl phosphoramide thioate, 4-amino-3,5,6-trichloropiclinic acid, 2,3-dichloro-1,4-naphthoquinone, dimethoxycarbonyl disulfide, 3-isopropyl-1H-2,1,3-benzothiadiazine-4(3H)-one-2,2-dioxide, 6,7-dihydrodipyridol[1,2-a:2':1'c] pyrazinium salt, 1,1'-dimethyl-4,4'-bipyridinium salt, 3,4,5,6-tetrahydro-3,5-dimethyl-2-thio-2H-1,3,5-thiadiazine, 1,2-dimethyl-3,5-diphenylpyrazolinium methyl sulfate, N-sec-butyl-2,6-dinitro-3,4-xylidine, N-sec.-butyl-4-t-butyl-2,6-dinitroaniline, $N^3,N^3$-diethyl-2,4-dinitro-6-trifluoromethyl-1,3-phenylenediamine, 1,1,1-trifluoro(4'-phenylsulfonyl)-methane sulfono-O-toluidine, 2-(1-naphthoxy)-N,N-diethyl propionamide, 2-t-butyl-4-(2,4-dichloro-5-isopropoxyphenyl)-1,3,4-oxadiazoline-5-one, 4-chloro-5-methylamino-2-(α,α,α-trifluoro-m-tolyl)-3(2H)-pyridazinone, N-cyclopropylmethyl-α,α,α-trifluoro- 2,6-dinitro-N-propyl-p-toluidine and N-phosphonomethyl glycine, etc.

When the other herbicide described is mixed with the compound of the present invention, the ratio of the compounds and the dose of the compounds are selected depending upon the selectivities and herbicidal effects of the compounds to the crop plants and the control of noxious weeds treated with them.

Certain examples of the preparations of the herbicidal compositions will be illustrated, however, the kinds and the ratio of the adjuvants are not limited and can be varied from the conventional consideration of the herbicidal compositions.

COMPOSITION NO. 1: WETTABLE POWDER

Compound No. 1—30 wt. %
Sodium higher alcohol sulfate—5 wt. %
Clay—65 wt. %

These components were uniformly mixed and pulverized to prepare a wettable powder.

COMPOSITION NO. 2: EMULSIFIABLE CONCENTRATE

Compound No. 2—25 wt. %
Polyoxyethylenealkylaryl ether—10 wt. %
Calcium dinaphthylmethanesulfonate—5 wt. %
Xylene—60 wt. %

These components were uniformly mixed to prepare an emulsifiable concentrate.

COMPOSITION NO. 3: GRANULES

Compound No. 3—3 wt. %
Bentonite—40 wt. %
Clay—50 wt. %
Sodium lignin sulfonate—7 wt. %

These components were uniformly mixed and pulverized and then, kneaded with water and granulated and dried to prepare granulates.

COMPOSITION NO. 4: DUST

Compound No. 4—2 wt. %
Clay—98 wt. %

The components were mixed and pulverized to prepare a dust.

COMPOSITION NO. 5: WETTABLE POWDER

Compound 5—30 wt. %
Kaolin—43 wt. %
White carbon—20 wt. %
Polyvinyl alcohol—5 wt. %
Polyoxyethylenenonylphenol—2 wt. %

These components were uniformly mixed and pulverized to prepare a wettable powder.

COMPOSITION NO. 6: EMULSIFIABLE CONCENTRATE

Compound 6—50 wt. %
Polyoxyethylenenonylphenol—5 wt. %
Alkylarylsulfonate—40 wt. %
Xylene—40 wt. %

These components were uniformly mixed to prepare an emulsifiable concentrate.

COMPOSITION NO. 7: GRANULES

Compound 7—5 wt. %
Siliceous sand—92 wt. %
White carbon—3 wt. %

These components were uniformly mixed and pulverized and then, kneaded with water and granulated and dried to prepare granulate.

COMPOSITION NO. 8: DUST

Compound 8—3 wt. %
White carbon—2 wt. %
Kaolin—95 wt. %

These components were mixed and pulverized to prepare a dust.

The herbicidal activity of the compounds of the present invention will be further illustrated by certain experimental tests.

EXPERIMENT 1

Test for crop plants and up-land weeds in pre-emergence (pre-germination) soil treatment.

Each pot of 600 cm$^2$ was filled with up-land soil and seeds of wheat, barley, soybean, radish, barnyard grass and large crab grass were sown in a depth of 0.5 cm. Each emulsifiable concentrate prepared in accordance with the method of Composition No. 2 was diluted with water to give the specific concentration of the compound for the application of 1 Klit./ha. and the diluted solution was uniformly sprayed on the soil surface.

Twenty days after the treatment, the herbicidal effect and the phytotoxicity of the crop plants were observed and rated as follows:

Herbicidal effect or phytotoxicity

10: Complete growth suppression is found;
9: Growth suppression of from 90 to 100%;
8: Growth suppression of from 80 to 90%;
7: Growth suppression of from 70 to 80%;
6: Growth suppression of from 60 to 70%;
5: Growth suppression of from 50 to 60%;
4: Growth suppression of from 40 to 50%;
3: Growth suppression of from 30 to 40%;
2: Growth suppression of from 20 to 30%;
1: Growth suppression of from 0 to 20%;
0: No herbicidal effect.

| Wh.: | Wheat | Bar.: | Barley |
|---|---|---|---|
| So.: | Soybean | Ra.: | Radish |
| B.G.: | Barnyard Grass (panicum crus-galli linnaeus) | Cr.G.: | Large Crab Grass (digitaria sanguinalis scopoli) |

Table 1

Result of Test in pre-emergence soil treatment (pot test)

| Compound (active ingredient Kg/ha.) | Dose | Wh. | Bar. | So. | Ra. | B.G. | Cr.G. |
|---|---|---|---|---|---|---|---|
| Compound No. 1 | 0.5 | 0 | 0 | 0 | 0 | 10 | 10 |
|  | 0.25 | 0 | 0 | 0 | 0 | 10 | 10 |
| Compound No. 2 | 0.5 | 0 | 0 | 0 | 0 | 10 | 10 |
|  | 0.25 | 0 | 0 | 0 | 0 | 10 | 10 |
| Compound No. 3 | 0.5 | 0 | 0 | 0 | 0 | 10 | 10 |
|  | 0.25 | 0 | 0 | 0 | 0 | 10 | 10 |
| Compound No. 4 | 0.5 | 0 | 0 | 0 | 0 | 10 | 10 |
|  | 0.25 | 0 | 0 | 0 | 0 | 10 | 10 |
| Compound No. 5 | 0.5 | 0 | 0 | 0 | 0 | 10 | 10 |
|  | 0.25 | 0 | 0 | 0 | 0 | 10 | 10 |
| Compound No. 6 | 0.5 | 0 | 0 | 0 | 0 | 10 | 10 |
|  | 0.25 | 0 | 0 | 0 | 0 | 10 | 10 |
| Compound No. 7 | 0.5 | 0 | 0 | 0 | 0 | 10 | 10 |
|  | 0.25 | 0 | 0 | 0 | 0 | 10 | 10 |
| Compound No. 8 | 0.5 | 0 | 0 | 0 | 0 | 10 | 10 |
|  | 0.25 | 0 | 0 | 0 | 0 | 10 | 10 |
| Compound | 0.5 | 0 | 0 | 0 | 0 | 10 | 10 |

Table 1-continued

Result of Test in pre-emergence soil treatment (pot test)

| Compound (active ingredient Kg/ha.) | Dose | Wh. | Bar. | So. | Ra. | B.G. | Cr.G. |
|---|---|---|---|---|---|---|---|
| No. 9 | 0.25 | 0 | 0 | 0 | 0 | 10 | 10 |
| Compound | 0.5 | 0 | 0 | 0 | 0 | 10 | 10 |
| No. 10 | 0.25 | 0 | 0 | 0 | 0 | 10 | 10 |
| Reference | 0.5 | 0 | 0 | 0 | 0 | 5 | 6 |
| Compound (A) | 0.25 | 0 | 0 | 0 | 0 | 1 | 3 |

Reference Compound (A)

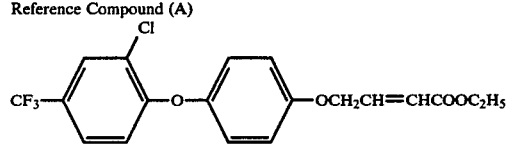

The results obtained by using each of the Compound Nos. 11 to 26 were substantially similar to those of the Compound Nos. 1 to 10.

EXPERIMENT 2

Test for crop plants and up-land weeds in pre-emergence soil treatment.

Each polyethylene pot of 2,000 cm$^2$ was filled with up-land soil and seeds of rice, maize, wheat, soybean, cotton, radish, barnyard grass, large crab grass, dent foxtail, johnson grass and goose foot (25 seeds for each plant) were sown in a depth of 0.5 cm.

Each emulsifiable concentrate prepared in accordance with the method of Composition No. 2 was diluted with water to give 0.25, 0.125 and 0.625 Kg/ha. of the active ingredient, and the diluted solution was uniformly sprayed on the surface of the soil at a rate of 200 ml per one pot.

Twenty days after the treatment, the herbicidal effect and the phytotoxicity of the crop plants were observed and rated as described above.

Ric.: Rice
Mai.: Maize
Wh.: Wheat
So.: Soybean
Cot.: Cotton
Ra.: Radish
B.G.: Barnyard Grass (*panicum crus-galli linnaeus*)
Cr.G.: Large Crab Grass (*digitaria sanguinalis scopoli*)
D.F.: Dent Foxtail (*alopecurus aequalis sobolewski* var. *amurensis ohwi*)
J.G.: Johnson Grass (*sorghum halepense*)
G.F.: Goose Foot (*chenopodium album linnaeus* var. *centrorubrum makino*)

Table 2

Result of Test in pre-emergence soil treatment (pot test):

| Compound (active ingredient Kg/ha.) | Dose | Ric. | Mai. | Wh. | So. | Cot. | Ra. | B.G. | Cr.G. | D.F. | J.G. | G.F. |
|---|---|---|---|---|---|---|---|---|---|---|---|---|
| Compound No. 1 | 0.25 | 8 | 6 | 0 | 0 | 0 | 0 | 10 | 10 | 10 | 10 | 0 |
|  | 0.125 | 7 | 1 | 0 | 0 | 0 | 0 | 10 | 10 | 10 | 10 | 0 |
|  | 0.0625 | 2 | 0 | 0 | 0 | 0 | 0 | 9 | 10 | 10 | 10 | 0 |
| Compound No. 2 | 0.25 | 8 | 7 | 0 | 0 | 0 | 0 | 10 | 10 | 10 | 10 | 0 |
|  | 0.125 | 6 | 2 | 0 | 0 | 0 | 0 | 10 | 10 | 10 | 10 | 0 |
|  | 0.0625 | 3 | 0 | 0 | 0 | 0 | 0 | 9 | 10 | 10 | 10 | 0 |
| Compound No. 3 | 0.25 | 6 | 4 | 0 | 0 | 0 | 0 | 10 | 10 | 10 | 10 | 0 |
|  | 0.125 | 3 | 0 | 0 | 0 | 0 | 0 | 10 | 10 | 10 | 10 | 0 |
|  | 0.0625 | 0 | 0 | 0 | 0 | 0 | 0 | 9 | 10 | 10 | 10 | 0 |
| Compound No. 4 | 0.25 | 4 | 3 | 0 | 0 | 0 | 0 | 10 | 10 | 10 | 10 | 0 |
|  | 0.125 | 2 | 0 | 0 | 0 | 0 | 0 | 10 | 10 | 10 | 10 | 0 |
|  | 0.0625 | 0 | 0 | 0 | 0 | 0 | 0 | 8 | 10 | 10 | 10 | 0 |
| Compound No. 5 | 0.25 | 6 | 2 | 0 | 0 | 0 | 0 | 10 | 10 | 10 | 10 | 0 |
|  | 0.125 | 4 | 1 | 0 | 0 | 0 | 0 | 10 | 10 | 10 | 10 | 0 |
|  | 0.0625 | 1 | 0 | 0 | 0 | 0 | 0 | 8 | 10 | 10 | 10 | 0 |
| Compound No. 6 | 0.25 | 3 | 3 | 0 | 0 | 0 | 0 | 10 | 10 | 10 | 10 | 0 |
|  | 0.125 | 1 | 0 | 0 | 0 | 0 | 0 | 10 | 10 | 10 | 10 | 0 |
|  | 0.0625 | 0 | 0 | 0 | 0 | 0 | 0 | 8 | 6 | 8 | 8 | 0 |
| Compound No. 7 | 0.25 | 6 | 1 | 0 | 0 | 0 | 0 | 10 | 10 | 10 | 10 | 0 |
|  | 0.125 | 3 | 0 | 0 | 0 | 0 | 0 | 10 | 10 | 10 | 10 | 0 |
|  | 0.0625 | 1 | 0 | 0 | 0 | 0 | 0 | 8 | 10 | 10 | 10 | 0 |
| Compound No. 8 | 0.25 | 5 | 3 | 0 | 0 | 0 | 0 | 10 | 10 | 10 | 10 | 0 |
|  | 0.125 | 2 | 0 | 0 | 0 | 0 | 0 | 10 | 10 | 10 | 10 | 0 |
|  | 0.0625 | 0 | 0 | 0 | 0 | 0 | 0 | 9 | 10 | 10 | 9 | 0 |
| Compound No. 9 | 0.25 | 2 | 0 | 0 | 0 | 0 | 0 | 10 | 10 | 10 | 10 | 0 |
|  | 0.125 | 1 | 0 | 0 | 0 | 0 | 0 | 10 | 10 | 10 | 10 | 0 |
|  | 0.0625 | 0 | 0 | 0 | 0 | 0 | 0 | 9 | 10 | 10 | 10 | 0 |
| Compound No. 10 | 0.025 | 6 | 2 | 0 | 0 | 0 | 0 | 10 | 10 | 10 | 10 | 0 |
|  | 0.125 | 3 | 0 | 0 | 0 | 0 | 0 | 10 | 10 | 10 | 10 | 0 |
|  | 0.0625 | 0 | 0 | 0 | 0 | 0 | 0 | 8 | 10 | 10 | 10 | 0 |
| Reference Compound (A) | 0.25 | 0 | 0 | 0 | 0 | 0 | 0 | 2 | 3 | 2 | 0 | 0 |
|  | 0.125 | 0 | 0 | 0 | 0 | 0 | 0 | 0 | 0 | 0 | 0 | 0 |
|  | 0.0625 | 0 | 0 | 0 | 0 | 0 | 0 | 0 | 0 | 0 | 0 | 0 |
| Reference Compound (B) | 0.25 | 0 | 0 | 0 | 0 | 0 | 0 | 1 | 2 | 1 | 0 | 0 |
|  | 0.125 | 0 | 0 | 0 | 0 | 0 | 0 | 0 | 0 | 0 | 0 | 0 |
|  | 0.0625 | 0 | 0 | 0 | 0 | 0 | 0 | 0 | 0 | 0 | 0 | 0 |
| Reference Compound (C) | 0.25 | 0 | 0 | 0 | 0 | 0 | 0 | 4 | 5 | 2 | 1 | 0 |
|  | 0.125 | 0 | 0 | 0 | 0 | 0 | 0 | 1 | 2 | 0 | 0 | 0 |
|  | 0.0625 | 0 | 0 | 0 | 0 | 0 | 0 | 0 | 0 | 0 | 0 | 0 |
| Reference Compound | 0.25 | 0 | 0 | 0 | 0 | 0 | 0 | 3 | 4 | 2 | 1 | 0 |
|  | 0.125 | 0 | 0 | 0 | 0 | 0 | 0 | 0 | 0 | 0 | 0 | 0 |

Table 2-continued

Result of Test in pre-emergence soil treatment (pot test):

| Compound (active ingredient Kg/ha.) | Dose | Ric. | Mai. | Wh. | So. | Cot. | Ra. | B.G. | Cr.G. | D.F. | J.G. | G.F. |
|---|---|---|---|---|---|---|---|---|---|---|---|---|
| (D) | 0.0625 | 0 | 0 | 0 | 0 | 0 | 0 | 0 | 0 | 0 | 0 | 0 |

Note:
Reference Compound (A): The compound shown in Experiment 1.
Reference Compound (B):

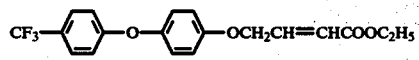

Reference Compound (C):

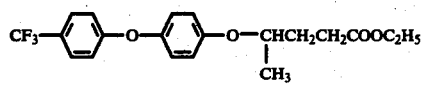

Reference Compound (D):

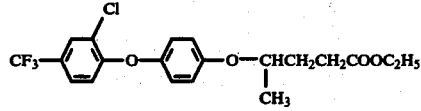

The results obtained by using each of the Compound Nos. 11 to 26 were substantially similar to those of the Compound Nos. 1 to 10.

EXPERIMENT 3

Test for crop plants and up-land weeds in (post-emergence germination) foliage treatment.

Each pot of 600 cm² was filled with up-land soil and seeds of corn, barley, soybean, radish, barnyard grass and large crab grass were sown.

Each emulsifiable concentrate prepared in accordance with the method of Composition No. 2 was diluted with water to give the specific concentration of the compound and the diluted solution was uniformly sprayed at a rate of 1 kl/ha, when the gramineous weeds were grown to 2 to 2.5 leaf stage and the broad-leaf weeds were grown to the first divergence stage.

Fifteen days from the treatment, the herbicidal effect and the phytotoxicity of the crop plants were observed and rated as described above.

Wh.: Wheat
Bar.: Barley
So.: Soybean
Ra.: Radish
B.G.: Barnyard Grass (*panicum crus-galli linnaeus*)
Cr.G.: Large Crab Grass (*digitaria sanguinalis scopoli*)

Table 3

Result of Test in Foliage Treatment (pot test):

| Compound (ppm) | Concentration | Wh. | Bar. | So. | Ra. | B.G. | Cr.G. |
|---|---|---|---|---|---|---|---|
| Compound No. 1 | 500 | 0 | 0 | 0 | 0 | 10 | 10 |
|  | 250 | 0 | 0 | 0 | 0 | 10 | 10 |
| Compound No. 2 | 500 | 0 | 0 | 0 | 0 | 10 | 10 |
|  | 250 | 0 | 0 | 0 | 0 | 10 | 10 |
| Compound No. 3 | 500 | 0 | 0 | 0 | 0 | 10 | 10 |
|  | 250 | 0 | 0 | 0 | 0 | 10 | 10 |
| Compound No. 4 | 500 | 0 | 0 | 0 | 0 | 10 | 10 |
|  | 250 | 0 | 0 | 0 | 0 | 10 | 10 |
| Compound No. 5 | 500 | 0 | 0 | 0 | 0 | 10 | 10 |
|  | 250 | 0 | 0 | 0 | 0 | 10 | 10 |
| Compound No. 6 | 500 | 0 | 0 | 0 | 0 | 10 | 10 |
|  | 250 | 0 | 0 | 0 | 0 | 10 | 10 |
| Compound No. 7 | 500 | 0 | 0 | 0 | 0 | 10 | 10 |
|  | 250 | 0 | 0 | 0 | 0 | 10 | 10 |
| Compound No. 8 | 500 | 0 | 0 | 0 | 0 | 10 | 10 |
|  | 250 | 0 | 0 | 0 | 0 | 10 | 10 |
| Compound No. 9 | 500 | 0 | 0 | 0 | 0 | 10 | 10 |
|  | 250 | 0 | 0 | 0 | 0 | 10 | 10 |
| Compound No. 10 | 500 | 0 | 0 | 0 | 0 | 10 | 10 |
|  | 250 | 0 | 0 | 0 | 0 | 10 | 10 |
| Reference (A) | 500 | 0 | 0 | 0 | 0 | 4 | 5 |
|  | 250 | 0 | 0 | 0 | 0 | 1 | 2 |
| Reference (B) | 500 | 0 | 0 | 0 | 0 | 3 | 4 |
|  | 250 | 0 | 0 | 0 | 0 | 1 | 1 |
| Reference (C) | 500 | 0 | 0 | 0 | 0 | 3 | 3 |
|  | 250 | 0 | 0 | 0 | 0 | 1 | 2 |
| Reference (D) | 500 | 0 | 0 | 0 | 0 | 2 | 2 |
|  | 250 | 0 | 0 | 0 | 0 | 0 | 1 |

Reference Compounds (A), (B), (C), (D)
The compounds shown in Experiment 2

The results obtained by using each of the Compound Nos. 11 to 26 were substantially similar to those of the Compound Nos. 1 to 10.

EXPERIMENT 4

Test for crop plants and up-land weeds in post-emergence foliage treatment.

Each polyethylene pot of 2,000 cm² was filled with up-land soil and seeds of rice, maize, wheat, soybean, cotton, radish, barnyard grass, crab grass, dent foxtail, johnson grass and goose foot (25 seeds for each plant) were sown.

Each emulsifiable concentrate prepared in accordance with the method of Composition No. 2 was diluted with water to give the concentration of 125, 62.5 and 31.25 ppm and the diluted solution was uniformly sprayed at a rate of 200 ml per pot, when the plants were grown to 2 to 4 leaf stages.

Ten days from the treatment, the herbicidal effect and the phytotoxicity of the crop plants were observed and rated as described above.

Ric.: Rice
Mai.: Maize
Wh.: Wheat
So.: Soybean
Cot.: Cotton
Ra.: Radish
B.G.: Barnyard Grass (*panicum crus-galli linnaeus*)

Cr.G.: Large Crab Grass (*digitaria sanguinalis scopoli*)
D.F.: Dent Foxtail (*alopecurus aequalis sobolewski* var. *amurensis ohwi*)
J.G.: Johnson Grass (*sorghum halepense*)
G.F.: Goose Foot (*chenopodium album linnaeus* var. *centrorubrum makino*)

liter/10 a. Then, the artificial rain was fallen under the rain fall condition by an artificial rain falling apparatus.

Observation:

The herbicidal degrees were observed at 15 days after the treatment and compared with those of the non-rain-falling sections.

Table 4

Result of Test in post-emergence foliage treatment (pot test):

| Compound | Concentration (ppm) | Ric. | Mai. | Wh. | So. | Cot. | Ra. | B.G. | Cr.G. | D.F. | J.G. | G.F. |
|---|---|---|---|---|---|---|---|---|---|---|---|---|
| Compound No. 1 | 125 | 8 | 4 | 0 | 0 | 0 | 0 | 10 | 10 | 10 | 10 | 0 |
|  | 62.5 | 2 | 2 | 0 | 0 | 0 | 0 | 10 | 10 | 10 | 10 | 0 |
|  | 31.25 | 0 | 0 | 0 | 0 | 0 | 0 | 9 | 10 | 10 | 10 | 0 |
| Compound No. 2 | 125 | 8 | 5 | 0 | 0 | 0 | 0 | 10 | 10 | 10 | 10 | 0 |
|  | 62.5 | 3 | 2 | 0 | 0 | 0 | 0 | 10 | 10 | 10 | 10 | 0 |
|  | 31.25 | 0 | 0 | 0 | 0 | 0 | 0 | 10 | 9 | 10 | 9 | 0 |
| Compound No. 3 | 125 | 3 | 2 | 0 | 0 | 0 | 0 | 10 | 10 | 10 | 10 | 0 |
|  | 62.5 | 0 | 0 | 0 | 0 | 0 | 0 | 10 | 10 | 10 | 10 | 0 |
|  | 31.25 | 0 | 0 | 0 | 0 | 0 | 0 | 10 | 10 | 10 | 10 | 0 |
| Compound No. 4 | 125 | 0 | 2 | 0 | 0 | 0 | 0 | 10 | 10 | 10 | 10 | 0 |
|  | 62.5 | 0 | 0 | 0 | 0 | 0 | 0 | 10 | 10 | 10 | 10 | 0 |
|  | 31.25 | 0 | 0 | 0 | 0 | 0 | 0 | 8 | 9 | 10 | 10 | 0 |
| Compound No. 5 | 125 | 4 | 2 | 0 | 0 | 0 | 0 | 10 | 10 | 10 | 10 | 0 |
|  | 62.5 | 0 | 1 | 0 | 0 | 0 | 0 | 10 | 10 | 10 | 10 | 0 |
|  | 31.25 | 0 | 0 | 0 | 0 | 0 | 0 | 8 | 9 | 9 | 10 | 0 |
| Compound No. 6 | 125 | 0 | 4 | 0 | 0 | 0 | 0 | 10 | 10 | 10 | 10 | 0 |
|  | 62.5 | 0 | 2 | 0 | 0 | 0 | 0 | 8 | 7 | 8 | 10 | 0 |
|  | 31.25 | 0 | 0 | 0 | 0 | 0 | 0 | 4 | 5 | 7 | 8 | 0 |
| Compound No. 7 | 125 | 4 | 1 | 0 | 0 | 0 | 0 | 10 | 10 | 10 | 10 | 0 |
|  | 62.5 | 2 | 0 | 0 | 0 | 0 | 0 | 10 | 10 | 10 | 10 | 0 |
|  | 31.25 | 0 | 0 | 0 | 0 | 0 | 0 | 10 | 9 | 10 | 10 | 0 |
| Compound No. 8 | 125 | 6 | 4 | 0 | 0 | 0 | 0 | 10 | 10 | 10 | 10 | 0 |
|  | 62.5 | 2 | 1 | 0 | 0 | 0 | 0 | 10 | 10 | 10 | 10 | 0 |
|  | 31.25 | 0 | 0 | 0 | 0 | 0 | 0 | 10 | 8 | 10 | 8 | 0 |
| Compound No. 9 | 125 | 3 | 0 | 0 | 0 | 0 | 0 | 10 | 10 | 10 | 10 | 0 |
|  | 62.5 | 0 | 0 | 0 | 0 | 0 | 0 | 10 | 10 | 10 | 10 | 0 |
|  | 31.25 | 0 | 0 | 0 | 0 | 0 | 0 | 10 | 9 | 9 | 10 | 0 |
| Compound No. 10 | 125 | 5 | 4 | 0 | 0 | 0 | 0 | 10 | 10 | 10 | 10 | 0 |
|  | 62.5 | 1 | 0 | 0 | 0 | 0 | 0 | 10 | 10 | 10 | 10 | 0 |
|  | 31.25 | 0 | 0 | 0 | 0 | 0 | 0 | 10 | 8 | 10 | 8 | 0 |
| Reference Compound (A) | 125 | 0 | 0 | 0 | 0 | 0 | 0 | 0 | 0 | 0 | 0 | 0 |
|  | 62.5 | 0 | 0 | 0 | 0 | 0 | 0 | 0 | 0 | 0 | 0 | 0 |
|  | 31.25 | 0 | 0 | 0 | 0 | 0 | 0 | 0 | 0 | 0 | 0 | 0 |
| Reference Compound (B) | 125 | 0 | 0 | 0 | 0 | 0 | 0 | 0 | 0 | 0 | 0 | 0 |
|  | 62.5 | 0 | 0 | 0 | 0 | 0 | 0 | 0 | 0 | 0 | 0 | 0 |
|  | 31.25 | 0 | 0 | 0 | 0 | 0 | 0 | 0 | 0 | 0 | 0 | 0 |
| Reference Compound (C) | 125 | 0 | 0 | 0 | 0 | 0 | 0 | 1 | 2 | 0 | 0 | 0 |
|  | 62.5 | 0 | 0 | 0 | 0 | 0 | 0 | 0 | 1 | 0 | 0 | 0 |
|  | 31.25 | 0 | 0 | 0 | 0 | 0 | 0 | 0 | 0 | 0 | 0 | 0 |
| Reference Compound (D) | 125 | 0 | 0 | 0 | 0 | 0 | 0 | 1 | 0 | 0 | 0 | 0 |
|  | 62.5 | 0 | 0 | 0 | 0 | 0 | 0 | 0 | 0 | 0 | 0 | 0 |
|  | 31.25 | 0 | 0 | 0 | 0 | 0 | 0 | 0 | 0 | 0 | 0 | 0 |

Reference compounds (A), (B), (C), (D)
The compounds shown in Experiment 2.

The results obtained by using each of the Compound Nos. 11 to 26 were substantially similar to those of the Compound Nos. 1 to 10.

RAIN ENDURANCE TEST

Weeds:
Barnyard grass: 3.8 to 4 leaf stage 21 to 25 cm
Large Crab grass: 3 to 3.5 leaf stage 5 to 10 cm
Active ingredient:
In accordance with the preparation No. 2, an emulsifiable concentrate was prepared by using compound No. 2.

Rain falling condition:
An artificial rain was fallen for 20 minutes at 30 min. 3 hours, 6 hours or 24 hours after the treatment in an amount of 5 mm.

Test methods:
A solution of the active ingredient at the specific concentration was uniformly sprayed at a rate of 100

Test results:
The herbicidal effect index was 5 in the case of rain-falling at 30 minutes after the treatment with 500 ppm of the solution to barnyard grass whereas the herbicidal effect index was 5 in the cases of non-rain-falling and rain-falling at 3 hours or more after the treatment with 500 ppm of the solution to barnyard grass.

The herbicidal effect index was 2.5 in all cases of rain-falling and non-rain-falling after the treatment with 100 ppm of the solution to large crab grass.

The rain endurance of the active ingredient was significantly high.

The herbicidal effect tests of the compounds no. 1, 2, 3, 4, 5, 6, 7, 8, 9 and 10 were carried out on an up-land field in which johnson grass and bermuda grass and other gramineous weeds such as crab grass and barnyard grass were naturally grown on 21st days after sowing soybean seeds by spraying each solution of each active ingredient at a ratio of 500 liter/ha. The leaf stages of weeds and soybean were as follows:

Soybean:—2 leaf-stage
Johnson grass:—2.5–4 leaf-stage
Bermuda grass:—5–6 leaf-stage
Large crab grass:—3.5–5 leaf-stage
Barnyard grass:—3.5–4 leaf-stage.

The herbicidal effects were excellent without any phototoxicity to soybean.

The herbicidal effect tests of the compounds no. 1, 2, 3, and 6 were carried out on an up-land field in which torpedo grass and paspalum grass and other gramineous weeds such as large crab grass and barnyard grass were naturally grown on 21st days after sowing cotton seeds by spraying each solution of each active ingredient at a ratio of 500 liter/ha. The leaf stages of weeds and cotton were as follows:

| Cotton: | 2 leaf-stage |
|---|---|
| Torpedo grass: (*panicum repens l.*) | 3.5–4 leaf-stage |
| Paspalum grass: (*paspalum conjugatum berg*) | 3–4 leaf-stage |
| Large crab grass: (*digitaria sanguinalis scopoli*) | 3.5–4 leaf-stage |
| Barnyard grass: (*panicum crus-galli linnaeus*) | 3.5–4 leaf-stage |

The herbicidal effects were excellent without any phytotoxicity to cotton.

What is claimed is:

1. A trifluoromethylphenoxy phenoxy crotonic acid derivative having the formula

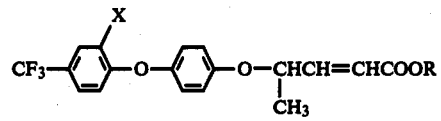

wherein X represents hydrogen or halogen atom, and R represents an alkyl, haloalkyl, alkenyl, haloalkenyl or alkynyl group.

2. A trifluoromethylphenoxy phenoxy crotonic acid derivative according to claim 1 wherein X represents hydrogen atom.

3. A trifluoromethylphenoxy phenoxy crotonic acid derivative according to claim 2 wherein R represents a lower alkyl group having 1 to 4 carbon atoms.

4. A trifluoromethylphenoxy phenoxy crotonic acid derivative according to claim 3 wherein R represents methyl or ethyl group.

5. A herbicidal composition which comprises a herbicidally effective amount of a trifluoromethylphenoxy phenoxy crotonic acid derivative having the formula

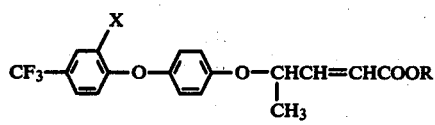

wherein X represents hydrogen or halogen atom and R represents an alkyl, haloalkyl, alkenyl, haloalkenyl or alkynyl group and an adjuvant.

6. A method of controlling undesired vegetation which comprises applying to the locus thereof an effective amount of a composition according to claim 5 as a soil or foliage treatment.

7. A method according to claim 6 wherein the active ingredient is applied at a rate of 0.01 to 10 Kg per 1 ha.

8. The method according to claim 6 wherein the active ingredient is applied at a diluted concentration of 10 to 10,000 ppm. in a foliage treatment.

* * * * *